US011814350B2

(12) United States Patent
Kendall et al.

(10) Patent No.: US 11,814,350 B2
(45) Date of Patent: Nov. 14, 2023

(54) METHODS FOR DISPROPORTIONATION QUENCHING OF OZONIDES

(71) Applicant: P2 SCIENCE, INC., Woodbridge, CT (US)

(72) Inventors: Alexander Kendall, Portland, OR (US); Yonghua Yang, Niantic, CT (US); Patrick Foley, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/286,651

(22) PCT Filed: Oct. 18, 2019

(86) PCT No.: PCT/US2019/057045
§ 371 (c)(1),
(2) Date: Apr. 19, 2021

(87) PCT Pub. No.: WO2020/082007
PCT Pub. Date: Apr. 23, 2020

(65) Prior Publication Data
US 2021/0371369 A1 Dec. 2, 2021

Related U.S. Application Data

(60) Provisional application No. 62/748,161, filed on Oct. 19, 2018.

(51) Int. Cl.
*C07C 67/313* (2006.01)
*C07C 45/40* (2006.01)
*C07C 51/09* (2006.01)

(52) U.S. Cl.
CPC ............ *C07C 67/313* (2013.01); *C07C 45/40* (2013.01); *C07C 51/09* (2013.01)

(58) Field of Classification Search
CPC ....... C07C 45/40; C07C 51/09; C07C 67/313; C07C 47/02; C07C 47/21; C07C 51/34; C07C 53/126; C07C 55/18; C07C 59/01; C07C 59/147; C07C 67/333; C07C 69/48; C07C 69/716; C02F 1/78; C07D 323/02
See application file for complete search history.

(56) References Cited

U.S. PATENT DOCUMENTS

| | | | |
|---|---|---|---|
| 2,813,113 A | | 11/1957 | Goebel et al. |
| 2,819,279 A | * | 1/1958 | Brown ............... C07C 45/40 562/544 |
| 3,023,244 A | | 2/1962 | Eschinasi |
| 3,664,810 A | * | 5/1972 | Tikhonovich ........... C07C 45/40 568/309 |
| 3,699,169 A | | 10/1972 | Bertele et al. |
| 3,856,833 A | * | 12/1974 | Siclari ................. C07C 45/40 562/577 |
| 4,296,258 A | | 10/1981 | Fehr et al. |
| 4,311,617 A | | 1/1982 | Ansari et al. |
| 4,491,537 A | | 1/1985 | Futoshi et al. |
| 4,791,228 A | | 12/1988 | Siclari et al. |
| 4,940,808 A | | 7/1990 | Schulz et al. |
| 5,292,941 A | | 3/1994 | Kigawa et al. |
| 5,543,565 A | | 8/1996 | McVay et al. |
| 5,756,821 A | | 5/1998 | Dilk et al. |
| 5,801,275 A | | 9/1998 | McVay et al. |
| 6,309,521 B1 | | 10/2001 | Andrews et al. |
| 6,395,695 B1 | | 5/2002 | Sivik |
| 6,512,131 B1 | | 1/2003 | Best et al. |
| 6,545,186 B2 | | 4/2003 | Giselbrecht et al. |
| 6,548,715 B1 | | 4/2003 | Bouillion et al. |
| 7,825,277 B2 | | 11/2010 | Gutsche et al. |
| 7,968,742 B2 | | 6/2011 | Aigner et al. |
| 8,221,708 B2 | | 7/2012 | Seebauer et al. |
| 9,035,091 B2 | | 5/2015 | Foley et al. |
| 9,604,898 B2 | | 3/2017 | Foley et al. |
| 9,682,914 B2 | | 6/2017 | Foley et al. |
| 9,701,606 B2 | | 7/2017 | Goeke et al. |
| 9,840,449 B2 | | 12/2017 | Foley et al. |
| 10,011,582 B2 | | 7/2018 | Foley et al. |
| 10,071,941 B2 | | 9/2018 | Foley et al. |
| 10,071,944 B2 | | 9/2018 | Foley et al. |
| 10,280,131 B2 | | 5/2019 | Foley et al. |
| 10,668,446 B2 | | 6/2020 | Foley et al. |
| 10,696,605 B2 | | 6/2020 | Foley et al. |
| 2003/0078453 A1 | | 4/2003 | Springer et al. |

(Continued)

FOREIGN PATENT DOCUMENTS

| | | |
|---|---|---|
| CA | 2247662 A1 | 3/1999 |
| CN | 102351697 A | 2/2012 |

(Continued)

OTHER PUBLICATIONS

Burckhardt, H., et al., "Oxy-aldehyde (VII.)," *Berichte Der Deutschen Chemischen Gesellschaft Abteilung B:Abhandlungen*, vol. 57, No. 10, pp. 1911-1917, (1924); Retrieved from the Internet: https://api.wiley.com/onlinelibrary/tdm/v1/articles/10.1002%2Fcber.19240571024 [retrieved on Jan. 23, 2006].

Cermak, et al., "Synthesis of 8-Stearolactone from Oleic Acid," *JAOCS*, vol. 77, No. 3, pp. 243-248, (2000).

Chmielewski, et al., "Organic Syntheses Under High Pressure. 3. General Approach to the Synthesis of Naturally Occuring .delta.-lactones," *The Journal of Organic Chemistry*, vol. 46, No. 11, pp. 2230-2233, (1981).

Cook, et al., "Study of the Total Synthesis of (-)-Exiguolide," *J. Org. Chem.*, vol. 77, pp. 6728-6742, (2012).

Cornforth, et al., "Studies of Cholesterol Biosynthesis 1. A New Chemical Degradation of Cholesterol," *Biochemical Journal*, vol. 54, pp. 590-597, (1953).

Dupe, et al., "Methyl Ricinoleate as Platform Chemical for Simultaneous Production of Fine Chemicals and Polymer Precursors," *ChemSusChem.*, vol. 5, pp. 2249-2254, (2012).

(Continued)

*Primary Examiner* — Yevgeny Valenrod
*Assistant Examiner* — Blaine G Doletski
(74) *Attorney, Agent, or Firm* — Hoxie & Associates LLC

(57) ABSTRACT

The present disclosure provides improved methods of performing ozonolysis on alkenes comprising non-reductive quenching of ozonide intermediates using Bronsted bases to yield aldehyde, ketone and/or carboxylic acid products.

11 Claims, No Drawings

(56) References Cited

U.S. PATENT DOCUMENTS

| | | |
|---|---|---|
| 2003/0100781 A1 | 5/2003 | Springer et al. |
| 2004/0186042 A1 | 9/2004 | Schmaus et al. |
| 2007/0010688 A1 | 1/2007 | Ko et al. |
| 2007/0142666 A1 | 6/2007 | Himeno et al. |
| 2007/0276165 A1 | 11/2007 | Gutsche et al. |
| 2009/0221083 A1 | 9/2009 | White et al. |
| 2010/0152479 A1 | 6/2010 | Seebauer et al. |
| 2012/0053354 A1 | 3/2012 | Yosida |
| 2013/0078685 A1 | 3/2013 | Ulrich et al. |
| 2013/0177497 A1 | 7/2013 | Fitch et al. |
| 2013/0240781 A1* | 9/2013 | Subramaniam .......... C01B 13/10 252/182.32 |
| 2013/0338150 A1 | 12/2013 | Boehme et al. |
| 2014/0316149 A1 | 10/2014 | Wickens et al. |
| 2014/0357547 A1 | 12/2014 | Goeke et al. |
| 2017/0247314 A1 | 8/2017 | Foley et al. |

FOREIGN PATENT DOCUMENTS

| | | |
|---|---|---|
| GB | 810571 * | 3/1959 |
| GB | 2043067 A | 10/1980 |
| JP | 2001-190947 A | 7/2001 |
| WO | WO 2009/061806 | 5/2009 |
| WO | WO 2015/027341 | 3/2015 |
| WO | WO 2016/091895 | 6/2016 |

OTHER PUBLICATIONS

Gross, R.A., Jr., "Ozonolysis Problems That Promote Student Reasoning," *Journal of Chemical Education*, vol. 83, No. 4, pp. 604-609, (2006).

Harding, et al., "beta-Methyl-delta-dodecadiene and beta-Methyl-delta-decadiene," *Journal of the Chemical Society*, Transactions, pp. 448-451, (1911).

Hearn, et al., "Kinetics and Product Studies for Ozonolysis Reactions of Organic Particles Using Aerosol CIMS," *The Journal of Physical Chemistry A*, vol. 108, No. 45, pp. 10019-10029, (2004).

Hon et al., "A Convenient and Efficient Workup of Ozonolysis Reactions Using Triethylamine," *Synthetic Communications*, vol. 23 (11), p. 1543-53, (1993).

Hon et al., "The mechanistic study and synthetic applications of the base treatment in the ozonolytic reactions," *Tetrahedron*, vol. 51 (17), p. 5019-34, (1995).

Griesbaum et al., "Ozonolysis of tetrasubstituted ethylenes, cycloolefins, and conjugated dienes on polyethylene," *The Journal of Organic Chemistry*, vol. 54 (2), p. 383-389, (1989).

Kadesch, R.G., "Ozonolysis of Fatty Acids and Their Derivatives," *Progress in the Chemistry of Fats and Other Lipids*, vol. 6, pp. 291-312, (1963).

Kula, et al., "Synthesis of Enantiomerically Pure Volatile Compounds Derived From (R)-3-Hydroxynonanal," *Tetrahedron: Asymmetry*, vol. 11, pp. 943-950, (2000).

Li, X., et al., "The Conversion of 5-hydroxymethyl Furfural (HMF) to Maleic Anhydride with Vanadium-based Heterogeneous Catalysts," *Green Chem.*, vol. 18, pp. 643-647, (2016).

Maggiolo, A. "Ozonization of Fatty Acids and Their Derivatives," *The Journal of the American Oil Chemists' Society*, vol. 40, pp. 161-164, (1963).

Miura et al., "Synthesis, x-ray analysis, and acidolysis of exo- and endo-1-methylindene ozonides," *Journal of the American Chemical Society*, vol. 105 (8), p. 2414-26, (1983).

Omonov, et al., "The Production of Biobased Nonanal by Ozonolysis of Fatty Acids," *RSC Adv.*, vol. 4, pp. 53617-53627, (2014); DOI: 10.1039/c4ra07917e.

Petit, et al., "Stereoselective Synthesis of Optically Active α-methyl Esters," *Tetrahedron Letters*, vol. 31, No. 15, pp. 2149-2152, (1990); Abstract Only.

Quan, et al., "A Convenient Protecting Group for Aldehydes," *Synlett*, vol. 2001, No. 12, pp. 1925-1926, (2001).

Rani, et al., "Ozonolysis of Oleic Acid Over a Nano Vanadium Pentoxide (V2O5) Catalyst," *European Journal of Scientific Research*, vol. 24, No. 3, pp. 428-432, (2008).

Richardson, et al., "A Practical Synthesis of Long-Chain Iso-Fatty Acids (iso-C 12-C19) and Related Natural Products," *Beilstein Journal of Organic Chemistry*, vol. 9, pp. 1807-1812, (2013).

Schiaffo, C.E., "I. An Improved Procedure for Alkene Ozonolysis. II. Expoloring a New Structural Paradigm for Peroxide Antimalarials," *Student Research Projects, Dissertations, and Theses—Chemistry, Department, University of Nebraska-Lincoln*, (Jun. 2011), Paper 23.

Shao, et al., "Asymmetric Hydrogenation of 3,5-Dioxoesters Catalyzed by Ru-binap Complex: A Short Step Asymmetric Synthesis of 6-Substituted 5,6-dihyrdo-2-pyrones," *Tetrahedron*, vol. 49, No. 10, pp. 1997-2010, (1993).

Willand-Charnley, et al., "Pyridine is an Organocatalyst for the Reactive Ozonolysis of Alkenes," *Org. Lett.*, vol. 14, No. 9, pp. 2242-2245, (2012).

Yoshida et al., "Some reactions of stable ozonide derived from 4H-cyclopenta[def]phenanthrene," *Tetrahedron*, vol. 35 (19), p. 2237-41, (1979).

* cited by examiner

METHODS FOR DISPROPORTIONATION QUENCHING OF OZONIDES

CROSS-REFERENCE TO RELATED APPLICATIONS

This U.S. non-provisional application is national stage application filed under 35 U.S.C. § 371 of PCT International Application No. PCT/US2019/057045, filed on Oct. 18, 2019, which claims priority to and the benefit of U.S. Provisional Application Ser. No. 62/748,161, filed on Oct. 19, 2018, the contents of each of which are hereby incorporated by reference in their entireties.

FIELD OF INVENTION

The present disclosure pertains to improved methods of performing ozonolysis on alkenes in which quenching results in disproportionation of the intermediate secondary ozonide into both oxidized and reduced fragments, the method comprising treating the ozonide intermediate with a Bronsted base. In some embodiments, the alkene is a fatty acid or fatty acid ester.

BACKGROUND

Ozonolysis is an industrially useful transformation that involves the oxidation of an unsaturated carbon-carbon bond of an alkene using ozone. The reported mechanism (the "Criegee mechanism") begins with initial formation of a primary ozonide (1,2,3-trioxolane) intermediate which rapidly decomposes into a carbonyl compound and carbonyl oxide compound. This pair of initial intermediates recombine to form a more stable secondary ozonide (1,2,4-trioxolane), a structure featuring a peroxide bridge.

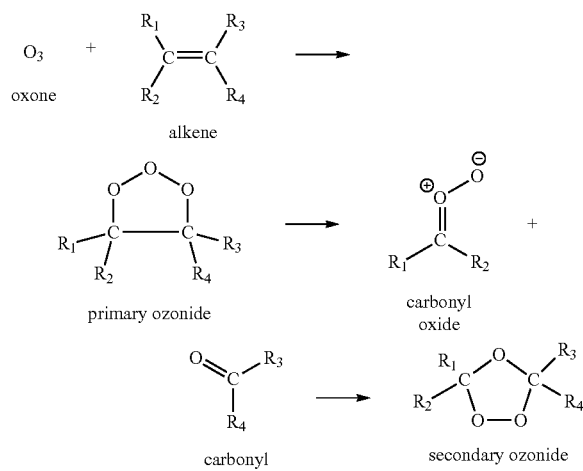

Although more stable than a primary ozonide or a carbonyl oxide, the secondary ozonide is still a high-energy chemical species subject to auto-accelerating thermal decomposition, decomposition to undesirable by-products, and organic peroxide formation (bis-peroxide, poly-peroxide, and hydroperoxide species). Therefore, further reactions must be carefully controlled in order to produce desired carbonyl product in good yield.

Uncontrolled thermal decomposition of secondary ozonides typically yields highly variable mixtures of products due to the strong driving force of peroxide bond decomposition (highly exothermic) and unselective kinetic pathways such as radical propagation. For these reasons, the secondary ozonide is an undesirable chemical product and must be reacted in a subsequent chemical step.

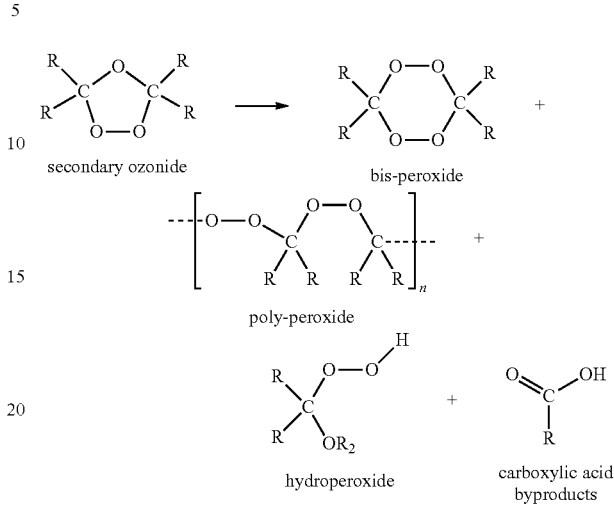

Traditionally, the secondary ozonide intermediates are either oxidatively or reductively cleaved to yield carbonyl products. Oxidative cleavage yields carboxylic acid and/or ketone products. Reductive cleavage yields ketone and/or aldehyde products, which may be further reduced to primary and secondary alcohol products. Traditional conditions cannot normally yield the combination of a carboxylic acid (an oxidation product) and an aldehyde (a reduction product). Carbonyl products, especially aldehydes, are highly desirable, but their high yield production is difficult because of over-reduction of these compounds to their alcohols. Because most commonly used reducing agents are capable of both secondary ozonide reduction and ketone or aldehyde reduction, the gentle reduction necessary to avoid over-reduction is difficult to achieve. Reaction conditions must also preserve the carbonyl products from known chemical incompatibilities and autooxidation, such as aldol condensation.

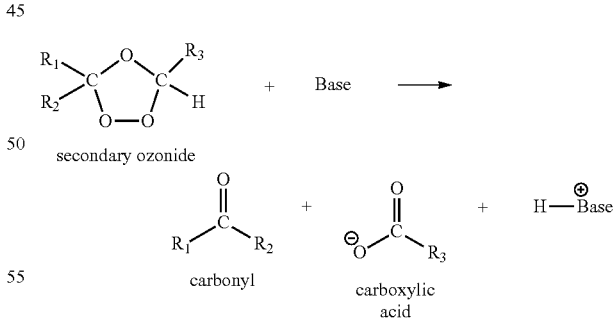

It has been reported that under certain conditions, the ozonide produced from a secondary or tertiary double bond can be quenched in a single step to yield a combination of a carbonyl (aldehyde or ketone) and a carboxylic acid. Thus, one carbon atom of the ozonide is formally oxidized, while the other is formally reduced—a disproportionation—because the carbon atom being oxidized is effectively reducing the other carbon atom—which dispenses with the need for an externally supplied oxidizing agent or reducing agent.

This reaction can be realized thermally, or can be pursued in the presence of certain metal catalysts such as vanadium or platinum. For example, Griesbaum et al. report the thermal disproportionation of the ozonide resulting from ozonolysis of cyclohexene and cyclooctene to yield 6-oxo-hexanonic acid and 8-oxo-octanoic acid, respectively. *J. Org. Chem.* 54, 383-89 (1989) (thermolysis at 60° C. in deuterochloroform). Yoshida et al. similarly disclose the thermolysis in refluxing toluene of the ozonide resulting from ozonolysis of 4H-cyclopenta[def]phenanthrene. *Tetrahedron* 35, 2237-41 (1979). Acidolysis has also been shown to effect the disproportionation of ozonides. Miura et al. report the acidolysis of the ozonides produced by ozonolysis of various methyl and phenyl substituted indenes using chlorosulfonic acid or acetic acid in dichloromethane. *J. Am. Chem. Soc.* 105, 2414-26 (1983). The results are variable and include multiple impurities and rearrangement by-products.

The uses of organic and inorganic bases to quench ozonides has shown mixed success. For example, Hon et al. describe the successful use of tertiary amine and heterocyclic amine bases in an E1cb elimination process to yield 5-oxopentanecarboxylic acids in high yield from the ozonide intermediate of cyclopentene ozonolysis. *Tetrahedron* 51(17), 5019-34 (1995); *Syn. Comm.* 23(11), 1543-53 (1993). However, when the reaction conditions were applied to the ozonides derived from styrene oxide and 1-decene, low yields and complex mixtures were obtained. Hon specifically describe that the use inorganic bases is less efficient.

There is a continuing need for rapid, safe means of quenching ozonide reaction streams to yield disproportionated products.

BRIEF SUMMARY OF THE INVENTION

The present disclosure provides a method of non-reductive quenching of ozonides using Bronsted bases to yield aldehyde, ketone and/or carboxylic acid products. The method is surprisingly simple, mild, and economical method. Suitable Bronsted bases include hydroxide and carboxylate bases. This invention greatly reduces the cost and complexity of ozonide quenching. Specifically, it provides a new reductant-free route to aldehydes directly from ozonides, which eliminates the risk of over-reduction of the resulting aldehydes to alcohols. This transformation is accomplished with inexpensive materials that improve product quality.

DETAILED DESCRIPTION OF THE INVENTION

It was discovered that ozonides generated from the reaction of alkenes with ozone can be treated with a Bronsted base to give fully quenched (no measurable peroxides) disproportionation products under mild conditions. Carboxylate salts, such as sodium acetate, sodium propionate, and/or sodium nonanoate, were found to be basic enough to facilitate the disproportionation. Furthermore, these salts could be generated in-situ through the addition of an inorganic base, such as sodium hydroxide, in an organic acid medium. A stoichiometric quantity of Bronsted base is necessary, unless the $pK_a$ of the resultant carboxylic acid from the disproportionation is within one $pK_a$ unit of the Bronsted base's conjugate acid (this allows the regeneration of Bronsted base through an acid-base equilibrium, $K_{eq}$), in which case the reaction can be facilitated with a catalytic amount of Bronsted base (typically 10-20%). This approach can yield ketones, aldehydes, and carboxylic acids in a facile manner.

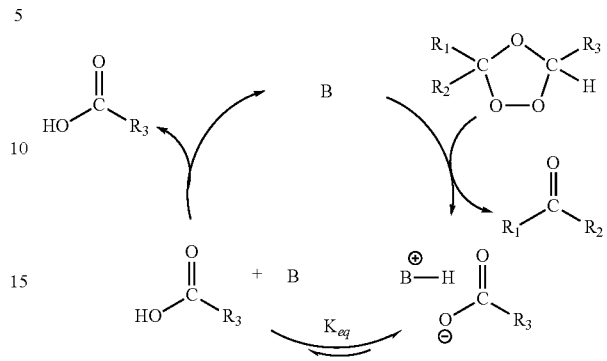

In a first aspect, the present disclosure therefore provides, a method (Method 1) of non-reductive quenching of ozonides using Bronsted bases to yield aldehyde, ketone and/or carboxylic acid products, wherein the method comprises (a) reacting an alkene with ozone to generate a secondary ozonide intermediate, and (b) quenching the ozonide using a Bronsted base to yield the aldehyde, ketone and/or carboxylic acid products.

In further embodiments of the first aspect, the present disclosure provides:

1.1 Method 1, wherein step (b) does not comprise a reducing agent and/or an oxidizing agent.

1.2 Method 1 or 1.1, wherein the Bronsted base of step (b) is an inorganic Bronsted base.

1.3 Method 1.2, wherein the inorganic Bronsted base is an alkali metal, alkaline earth metal or ammonium carboxylate salt (e.g., an acetate, propionate, or butyrate salt).

1.4 Method 1.3, wherein the inorganic Bronsted base is an alkali metal or alkaline earth metal salt of a $C_2$-$C_{12}$ saturated carboxylic acid (e.g., an acetate, propionate, butanoate, pentanoate, hexanoate, heptanoate, octanoate, nonanoate, or decanoate).

1.5 Method 1.3, wherein the inorganic Bronsted base is an alkali metal or alkaline earth metal fatty acid carboxylate (i.e., the alkali metal or alkaline earth metal salt of a fatty acid).

1.6 Method 1.5, wherein the fatty acid carboxylate is a $C_8$-$C_{26}$ fatty acid carboxylate (e.g., a $C_8$, $C_{10}$, $C_{12}$, $C_{14}$, $C_{16}$, $C_{18}$, $C_{20}$, $C_{22}$, $C_{24}$ or $C_{26}$ fatty acid carboxylate).

1.7 Method 1.5 or 1.6, wherein the fatty acid carboxylate is a saturated fatty acid carboxylate (e.g., caprylate, caprate, laurate, myristate, palmitate, stearate, arachidate, behenate, lignocerate or ceroate).

1.8 Method 1.5 or 1.6, wherein the fatty acid carboxylate is an unsaturated fatty acid carboxylate (e.g., myristoleate, pamitoleate, sapienate, oleate, elaidate, gadolaeate, eicosenoate, erucate, eicosadienoate, docosadienoate, linoleate, linolenate, stearidonate, arachidonate).

1.9 Method 1.2, wherein the inorganic Bronsted base is an alkali metal or alkaline earth metal hydroxide (e.g., sodium hydroxide, potassium hydroxide, calcium hydroxide, magnesium hydroxide).

1.10 Any of Methods 1.3-1.9, wherein the inorganic Bronsted base carboxylate salt is generated in-situ by performing step (b) using a mixture of the carboxylic acid and an alkali metal or alkaline earth metal hydroxide, carbonate, bicarbonate, phosphate, or sulfate.

1.11 Method 1.10, wherein step (b) comprises an excess of carboxylic acid (e.g., greater than 1 equivalent, or greater than 1.5 equivalents, or greater than 2 equivalents, or greater than 3 equivalents, or greater than 4 equivalents, or greater than 5 equivalents, or greater than 10 equivalents, or greater then 20 equivalents, or greater than 50 equivalents of the carboxylic acid, measured with respect to the theoretical molar amount of ozonide present in step (b).

1.12 Method 1.10 or 1.11, wherein the carboxylic acid is an unsaturated fatty acid and the unsaturated fatty acid is the alkene precursor to the ozonide.

1.13 Method 1.11, wherein the carboxylic acid is the solvent for step (b), e.g., wherein the solvent is a $C_{2-12}$ saturated carboxylic acid, or a $C_{8-26}$ saturated fatty acid.

1.14 Method 1.9, 1.10 or 1.11, wherein step (b) comprises 0.5 to 3 molar equivalents of the alkali metal or alkaline earth metal hydroxide, measured with respect to the theoretical molar amount of ozonide present in step (b), e.g., 1 to 2 equivalents or 1 to 1.5 equivalents or about 1 equivalent.

1.15 Any of Methods 1.9 to 1.14, wherein step (b) comprises a catalytic amount of the alkali or alkaline earth metal hydroxide, e.g., 0.1 to 0.9 molar equivalents of the alkali metal or alkaline earth metal hydroxide, measured with respect to the theoretical molar amount of ozonide present in step (b), e.g., 0.1 to 0.5 equivalents or 0.1 to 0.3 equivalents, or 0.1 to 0.2 equivalents, or about 0.1 equivalent.

1.16 Method 1 or any of 1.1-1.15, wherein step (b) does not comprise an organic Bronsted base (e.g., a trialkyl amine or heterocyclic amine base).

1.17 Method 1 or any of 1.1-1.16, wherein step (b) comprises water as a co-solvent.

1.18 Method 1 or any of 1.1-1.17, wherein step (b) occurs at a temperature from 30 to 100° C.

1.19 Method 1.18, wherein said temperature is between 50 and 90° C. or between 50 and 80° C.

1.20 Method 1, or any of 1.1-1.19, wherein the method further comprises isolating or purifying an aldehyde product from the quenching step (b).

1.21 Method 1, or any of 1.1-1.19, wherein the method further comprises isolating or purifying a ketone product from the quenching step (b).

1.22 Method 1, or any of 1.1-1.21, wherein the method further comprises isolating or purifying a carboxylic acid product from the quenching step (b).

1.23 Method 1, or any of 1.1-1.22, wherein the alkene is a monounsaturated fatty acid or ester, e.g., a $C_8$-$C_{26}$ monounsaturated fatty acid or ester.

1.24 Method 1.23, wherein the alkene is a $C_{10}$-$C_{20}$ monounsaturated fatty acid or ester.

1.25 Method 1.23, wherein the alkene is selected from oleic acid, ricinoleic acid, or erucic acid, or an ester thereof.

1.26 Method 1.23, 1.24 or 1.25, wherein the alkene is a fatty acid ester, e.g., a $C_{1-6}$ alkyl ester (e.g., a methyl or ethyl ester).

1.27 Method 1, or any of 1.1-1.22, wherein the alkene is a terpene.

1.28 Method 1.27, wherein the terpene is selected from pinenes, camphenes, citronellol, citronellal, isopulegol, longifolene, isothujone and thujone.

1.29 Any preceding method wherein the alkene is non-cyclic (e.g., the alkene is a linear alkene).

1.30 Any preceding method wherein the alkene has a disubstituted or trisubstituted double bond.

In a second aspect, the present disclosure provides for use of a Bronsted base in a method of non-reductive quenching of an ozonide, for example, a method according to Method 1 or any of 1.1-1.30.

In a third aspect, the present disclosure provides an aldehyde, ketone or carboxylic acid made according to Method 1 or any of 1.1-1.30.

In a fourth aspect, the present disclosure provides a product or composition comprising an aldehyde, ketone or carboxylic acid made according to Method 1 or any of 1.1-1.30.

For ozonides that have two geminal functional groups, the Bronsted base deprotonation can only occur at the carbon with an available hydrogen. That is to say, the disproportion is chemoselective when applied to trisubstituted ozonides and geminal disubstituted ozonides. For example, a representative disproportionation of β-pinene ozonide would result in roughly equimolar ratios of nopinone and formic acid. Vicinal disubstituted alkenes produce secondary ozonides that can undergo deprotonation at either one of the carbon centers of the 5-membered ozonide ring, resulting in mixtures of aldehyde and carboxylic acid products from each carbon (ratios dependent on the difference in $pK_a$ of the C—H bonds and the kinetics of deprotonation). Similarly, monosubstituted ozonides can disproportionate into a mixture of products in the same manner as ozonides from vicinal disubstituted alkenes. Thus, chemoselectivity for the disproportionation can be predicted for many substrates. Most notably, aldehydes can be obtained directly from secondary ozonides from the method of the present disclosure without the use of a reducing agent.

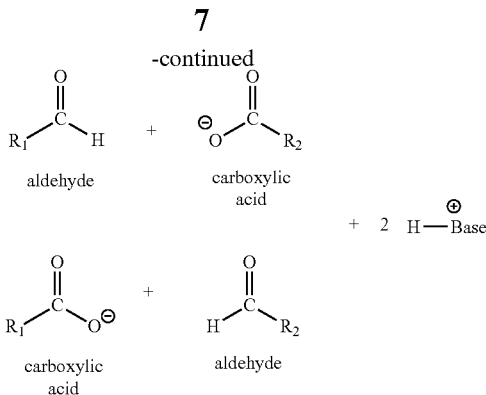

While this approach can be applied to a wide range of ozonides (any mono-, di-, or tri-substituted secondary ozonide), the ozonides of fatty acids and terpenes are particularly well suited for this transformation. The ozonides of oleic acid, ricinoleic acid, erucic acid, and their esters can be easily quenched using this approach, as can the ozonides of various terpenes including pinenes, camphenes, citronellol, citronellal, isopulegol, longifolene, isothujone, and thujone.

In some embodiments, the ozonides are generated in a mixture wherein the solvent comprises a $C_2$-$C_{26}$ carboxylic acid, for example a $C_{2-12}$ carboxylic acid or a $C_{8-26}$ fatty acid. In some embodiments, the solvent comprises acetic acid, propanoic acid, or nonanoic acid, or a combination thereof. In some embodiments, water is used as a co-solvent.

In some embodiments, the quenching takes place at a temperature between 30 and 100° C., preferably between 50 and 80° C.

By way of example, a representative disproportionation of oleic acid ozonide according to this method would result in roughly equimolar ratios of nonanal, nonanoic acid, 9-oxononanoic acid, and azelaic acid. Similarly, an erucic acid ozonide quenched by this method would result in roughly equimolar amounts of nonanal, nonanoic acid, 13-oxotridecanoic acid, and brassylic acid.

As used herein, the term "inorganic Bronsted base" refers to a basic salt formed between a Bronsted acid (the conjugate acid) and a neutral or near-neutral cation. As such, "inorganic Bronsted base" refers to any basic salt comprising the conjugate base of a Bronsted acid. Thus, "inorganic Bronsted base" includes, but is not limited to, hydroxide, sulfate, phosphate, carbonate, bicarbonate, and carboxylate salts (notwithstanding that carboxylic acids are often considered "organic" acids). "Inorganic Bronsted base" does not include non-ionic Bronsted bases, such as organic alkylamines (e.g., mono-, di- or tri-alkyl amines) or organic heterocycle bases (e.g., pyridines, pyrimidines).

As used herein, the term "alkali metal" includes lithium, sodium, potassium, and rubidium. As used herein, the term "alkaline earth metal" includes beryllium, magnesium, calcium, and strontium. While sodium salts are practical and efficient, lithium, potassium, magnesium, ammonium, and calcium salts can be used as well. And while hydroxide is also highly practical, other bases such as carbonates, and phosphates can be used to generate the desired species.

EXAMPLES

Example 1—Quenching of Oleic Acid Ozonide

To a 123 g solution of freshly prepared ozonide of oleic acid methyl ester (33 wt % oleic acid methyl ester in propionic acid, 1.08 mol/kg) is added 16 g of a 33 wt % solution of sodium hydroxide in water very slowly. The reaction mixture exothermically heats itself to 65° C., where the temperature is maintained by control of the addition rate of the sodium hydroxide solution. After 60 minutes at 65° C., the reaction mixture is found to contain less than 17 mmol/L peroxides (>95% conversion of ozonide) by iodometric titration indicating that the ozonide was consumed.

A 200 mg aliquot of the reaction mixture is sampled and digested by heating with 1.5 mL MeOH and 1.5 mL BF3.MeOH at 75° C. for 15 minutes to esterify the acids for GC analysis. GC analysis indicates a 1:1:1:1 ratio of four compounds—nonanal dimethyl acetal, nonanoic acid methyl ester, azelaic acid dimethyl ester, and methyl 9-oxononanoate dimethyl acetal.

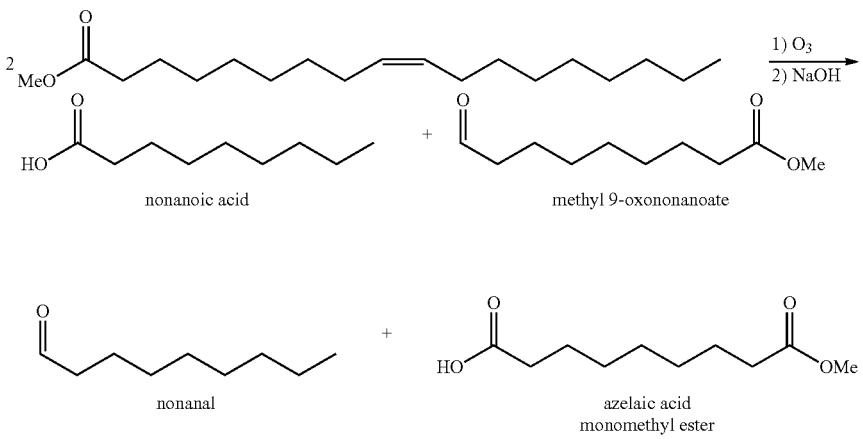

Example 2—Quenching of Ricinoleic Acid Ozonide

To a 49 g solution of freshly prepared ozonide of ricinoleic acid (33 wt % ricinoleic acid in propanoic acid, 1.12 mol/kg) is added 6.3 g of a 50 wt % solution of sodium hydroxide in water very slowly. The reaction mixture exothermically heats itself to 70° C., where the temperature is maintained by control of the addition rate of the sodium hydroxide solution. After 30 minutes at 70° C., the reaction mixture is found to contain less than 19 mmol/L peroxides (>95% conversion of ozonide) by iodometric titration indicating the ozonide was consumed A 200 mg aliquot of the reaction mixture was analyzed by GC as described in Example 2, and the results show a 1:1:1:1 ratio of four products: trans-2-nonenal dimethyl acetal, 3-hydroxynonanoic acid methyl ester, azelaic acid dimethyl ester, and methyl 9-oxononanoate dimethyl acetal.

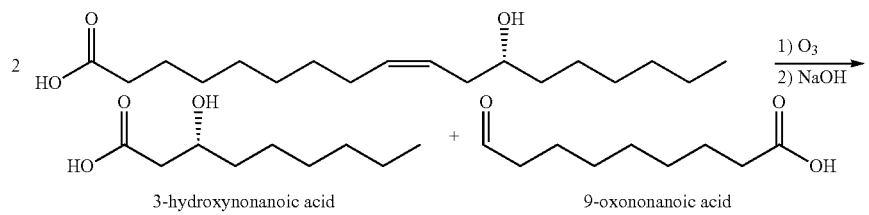

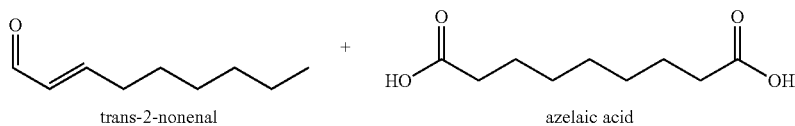

3-hydroxynonanoic acid     9-oxononanoic acid trans-2-nonenal     azelaic acid

The Examples provided herein are exemplary only and are not intended to be limiting in any way to the various aspects and embodiments of the invention described herein.

We claim:

1. A method of non-reductive quenching of ozonides using Brønsted bases to yield aldehyde and carboxylic acid, or ketone and carboxylic acid products, wherein the method comprises (a) reacting an alkene with ozone to generate a secondary ozonide intermediate, and (b) quenching the ozonide by adding an alkali metal or alkaline earth metal hydroxide, carbonate, bicarbonate, sulfate or phosphate to the ozonide in a $C_2$-$C_{12}$ carboxylic acid solvent with water co-solvent to form the corresponding alkali metal or alkaline earth metal salt of the $C_2$-$C_{12}$ carboxylate salt Brønsted base in-situ, to yield the aldehyde and carboxylic acid products, or the ketone and carboxylic acid products; and wherein step (b) does not comprise a reducing agent and/or an oxidizing agent.

2. The method of claim 1, wherein the $C_2$-$C_{12}$ carboxylic acid solvent is a $C_2$-$C_{12}$ saturated carboxylic acid.

3. The method of claim 1, wherein the alkali metal or alkaline earth metal hydroxide, carbonate, bicarbonate, sulfate or phosphate added in step (b) is an alkali metal or alkaline earth metal hydroxide.

4. The method of claim 3, wherein the alkali metal or alkaline earth metal hydroxide is selected from the group consisting of sodium hydroxide, potassium hydroxide, calcium hydroxide, and magnesium hydroxide.

5. The method of claim 1, wherein step (b) occurs at a temperature from 30 to 100° C., optionally, wherein said temperature is between 50 and 90° C. or between 50 and 80° C.

6. The method of claim 1, wherein the method further comprises isolating or purifying an aldehyde product and a carboxylic acid product, or a ketone product and a carboxylic acid product, from the quenching step (b).

7. The method of claim 1, wherein the alkene is a monounsaturated fatty acid or ester.

8. The method of claim 1, wherein the alkene is a terpene.

9. The method of claim 8, wherein the terpene is selected from pinenes, camphenes, citronellol, citronellal, isopulegol, longifolene, isothujone and thujone.

10. The method of claim 1, wherein the alkene is oleic acid, ricinoleic acid, erucic acid, or any esters thereof.

11. The method of claim 1, wherein the secondary ozonide is a monosubstituted, disubstituted, or trisubstituted ozonide, and the products comprise aldehyde or ketone product and carboxylic acid product.

* * * * *